Figure 1:
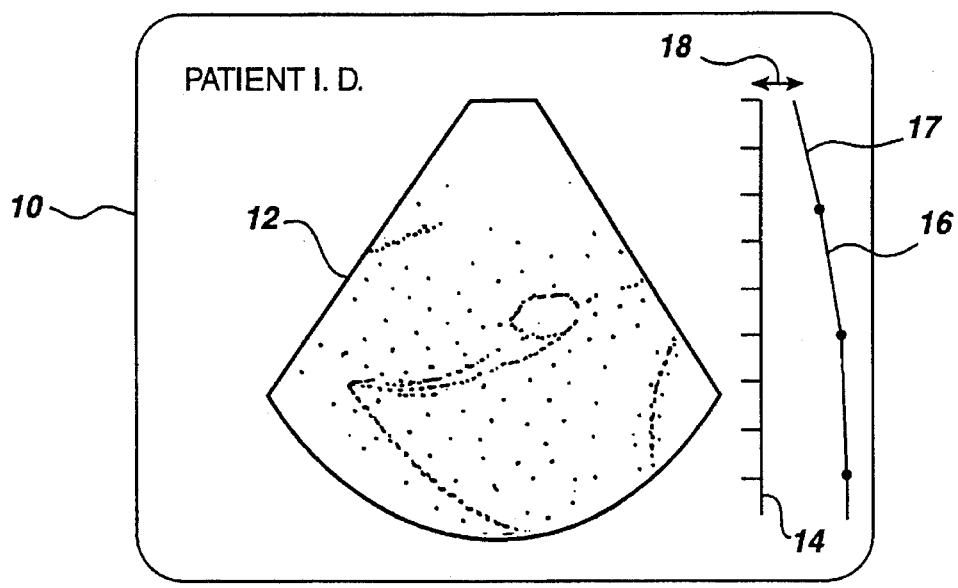

United States Patent [19]
Rust et al.

[11] Patent Number: 5,482,045
[45] Date of Patent: Jan. 9, 1996

[54] ULTRASONIC DIAGNOSTIC SYSTEM GAIN CONTROL

[75] Inventors: David W. Rust, Seattle; David N. Roundhill, Bothell, both of Wash.

[73] Assignee: Advanced Technology Laboratories, Inc., Bothell, Wash.

[21] Appl. No.: 321,482

[22] Filed: Oct. 12, 1994

[51] Int. Cl.⁶ ................................................ A61B 8/00
[52] U.S. Cl. ................................................ 128/661.01
[58] Field of Search .................. 128/660.02, 660.06, 128/660.07, 661.01, 661.03, 662.02; 73/625, 626, 599, 602, 642

[56] References Cited

U.S. PATENT DOCUMENTS

| | | | |
|---|---|---|---|
| 4,534,221 | 8/1985 | Fife et al. | 128/661.01 |
| 4,566,460 | 1/1986 | Sato et al. | 128/660.02 |
| 4,945,915 | 8/1990 | Nagasaki | 128/660.07 |
| 5,142,649 | 8/1992 | O'Donnell | 367/7 |
| 5,315,999 | 5/1994 | Kinicki et al. | 128/660.07 |
| 5,345,939 | 9/1994 | Engeler et al. | 128/661.01 |

*Primary Examiner*—George Manuel
*Attorney, Agent, or Firm*—W. Brinton Yorks, Jr.

[57] ABSTRACT

An ultrasonic diagnostic system is provided which automatically sets up the TGC characteristic to be used for a given ultrasound examination. Upon user selection of a particular ultrasound application, a setup controller accesses a predetermined TGC characteristic for the selected application. The predetermined TGC characteristic is used to control the gain of a TGC amplifier and is also displayed to the user. By adjustment of a series of TGC controls the user can vary the TGC characteristic from the predetermined characteristic.

8 Claims, 4 Drawing Sheets

ULTRASONIC DIAGNOSTIC SYSTEM GAIN CONTROL

This invention relates to improvements in ultrasonic diagnostic imaging systems, and in particular to techniques for controlling signal gain as a function of depth during reception of ultrasonic echo signals.

Ultrasonic imaging systems create images of the interior of a patient's body from echoes received in response to the transmission of ultrasonic waves into the body of the patient. Ultrasonic pulses are transmitted over a field of interest in the body along a plurality of beam direction, causing echoes to return from along each beam direction as the transmitted pulse encounters tissue structures and interfaces in the body. By mapping the received echoes as a function of their time of receipt and direction an image of the interior of the body can be assembled and displayed.

It is well known that as ultrasonic waves propagate through the body they are continually attenuated by their passage through the tissue of the body. Hence, echoes returning from increasing depths in the body will exhibit ever increasing attenuation. To compensate for this attenuation ultrasonic systems have traditionally amplified returning echoes as a function of depth. As echoes return from increasing depths they are processed by increasing amplification. Since the transmitted pulses proceed through the body with time and echoes return from increasing depths at increasing time periods following transmission of each pulse, this amplification is usually controlled by varying the gain of an amplifier in the ultrasound receiver as a function of the time following pulse transmission. This form of gain control is referred to as time gain compensation, or TGC.

It has been customary for an ultrasound system to have a row of gain setting switches which may be set by the user to adjust TGC. Each switch is an input to the TGC function generator which produces the TGC function over a portion of the reception period following pulse transmission. If there are five switches, for instance, five different variations in gain can be sequentially applied over the reception period during which echoes are received from the shallowest to the deepest depth. Usually the user will set these switches through a process of trial and error, viewing the image and moving the switches until the most pleasing image is obtained.

In order to provide efficiency in the time required to optimize an ultrasound system for a particular ultrasonic examination it would be preferable that the user not have to spend time experimentally setting the TGC controls. It would be desirable for TGC to be automated by the ultrasound system in a manner that is optimal for each type of ultrasound exam. But it would also be desirable for the user to be able to alter automated TGC settings to enable the TGC characteristic to be specifically tailored for the signal conditions encountered when examining particular patients.

In accordance with the principles of the present invention, a time gain compensation system is provided for an ultrasonic diagnostic instrument in which the time gain compensation settings are automatically provided by the instrument dependent upon the type of examination being performed by the physician. For each type of ultrasound examination procedure the system automatically sets the most desired TGC characteristic and displays the predetermined characteristic on the system's image display. Conventional TGC switches are provided, but are used only to vary the TGC characteristic from the predetermined characteristic. The alignment of the TGC switches is a visual reminder to the physician of changes which have been made to the predetermined characteristic.

Figure 2:
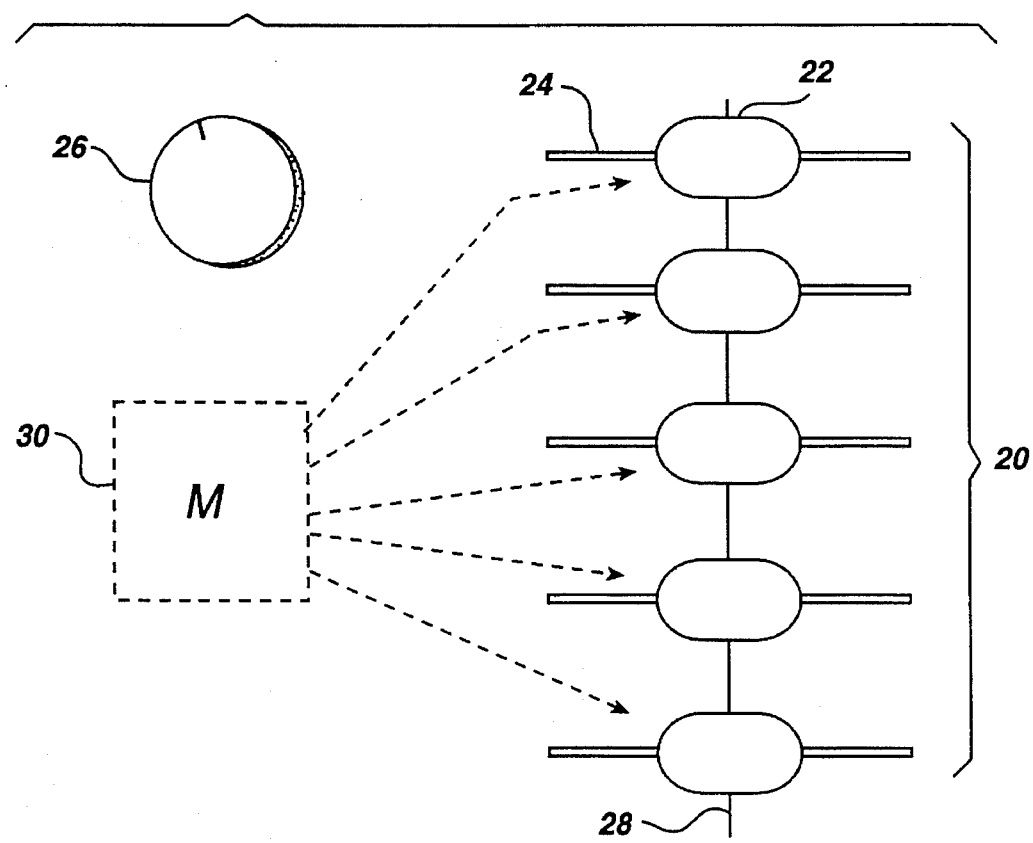
Figure 3:
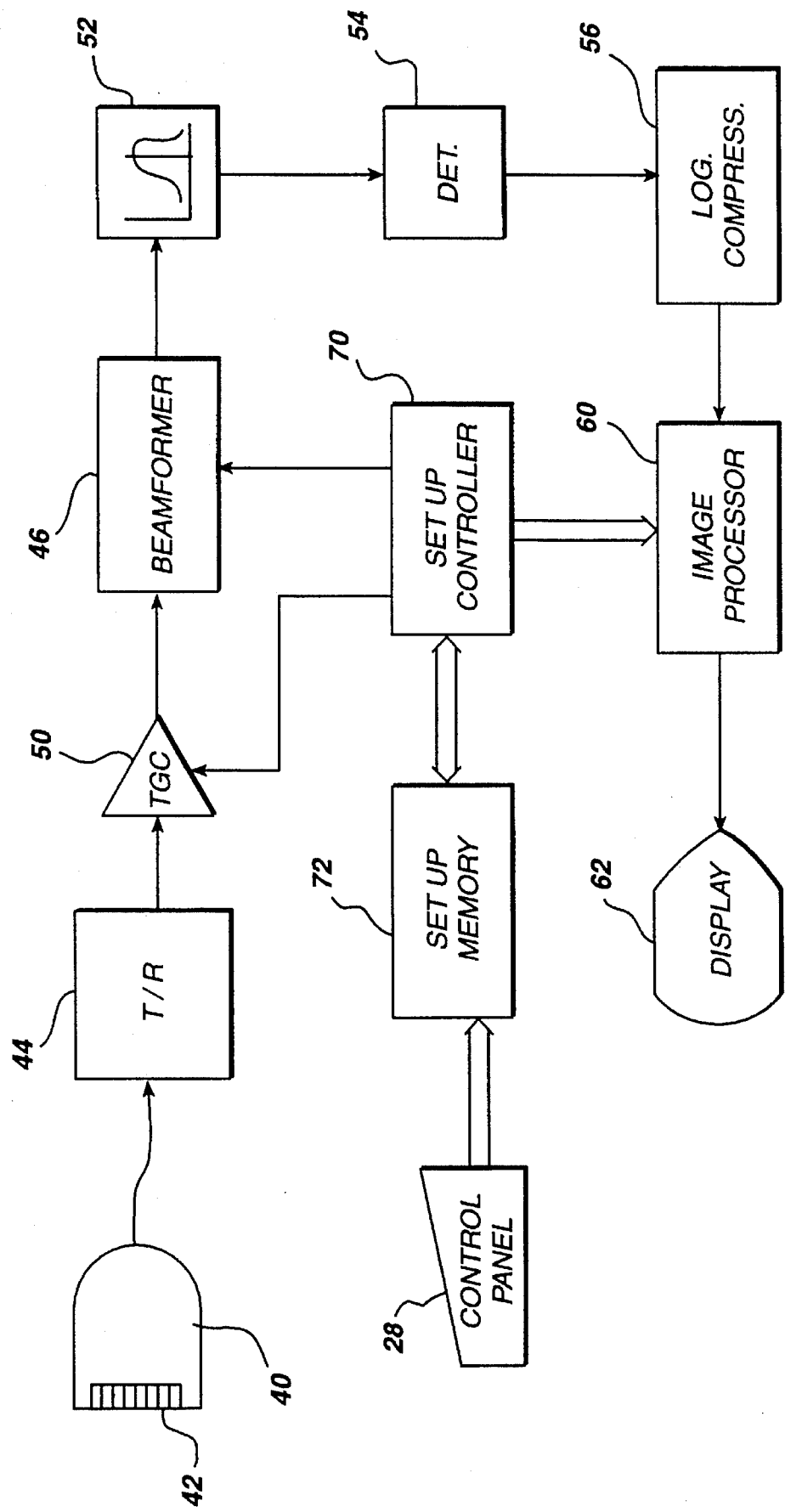
Figure 4:
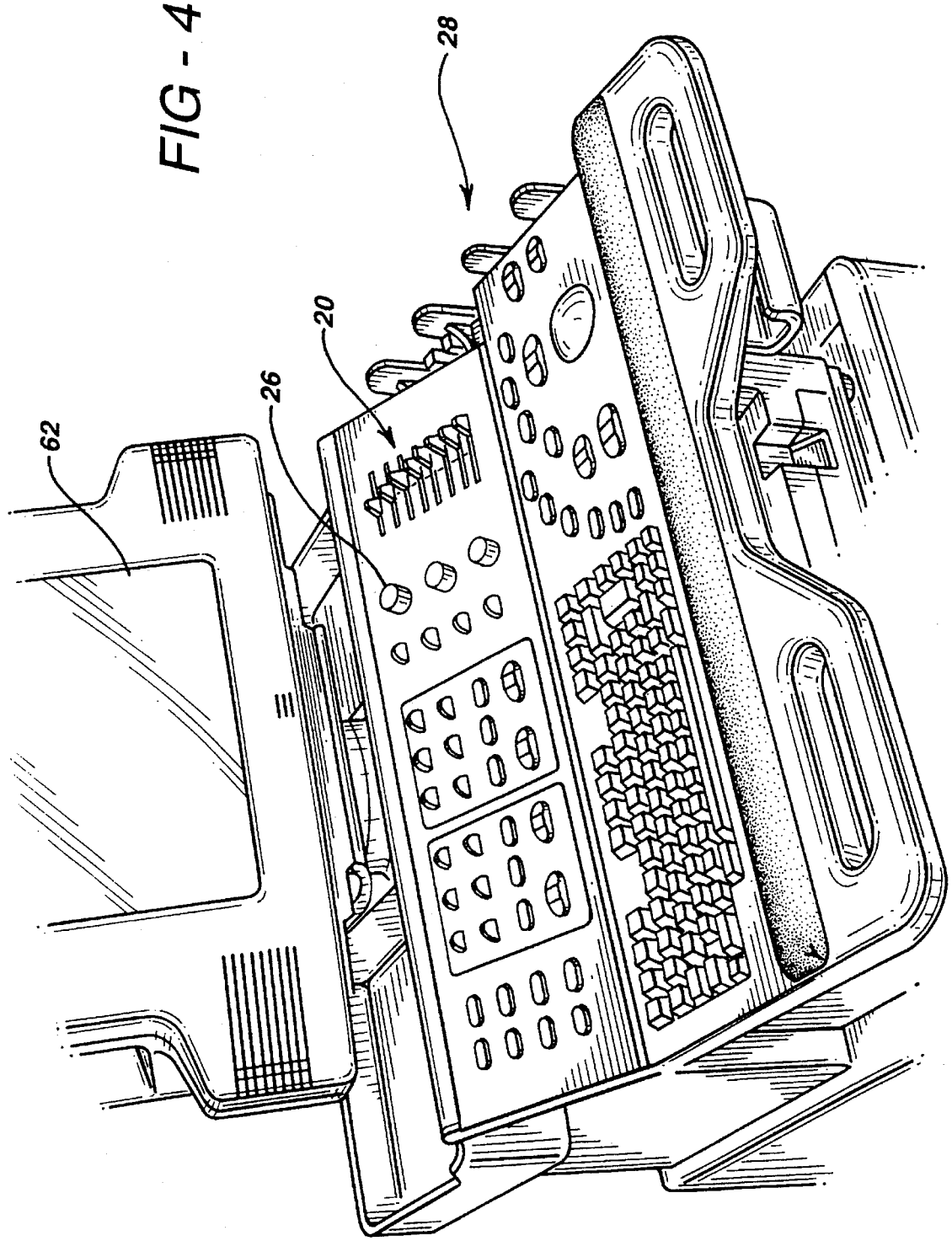
Figure 5:
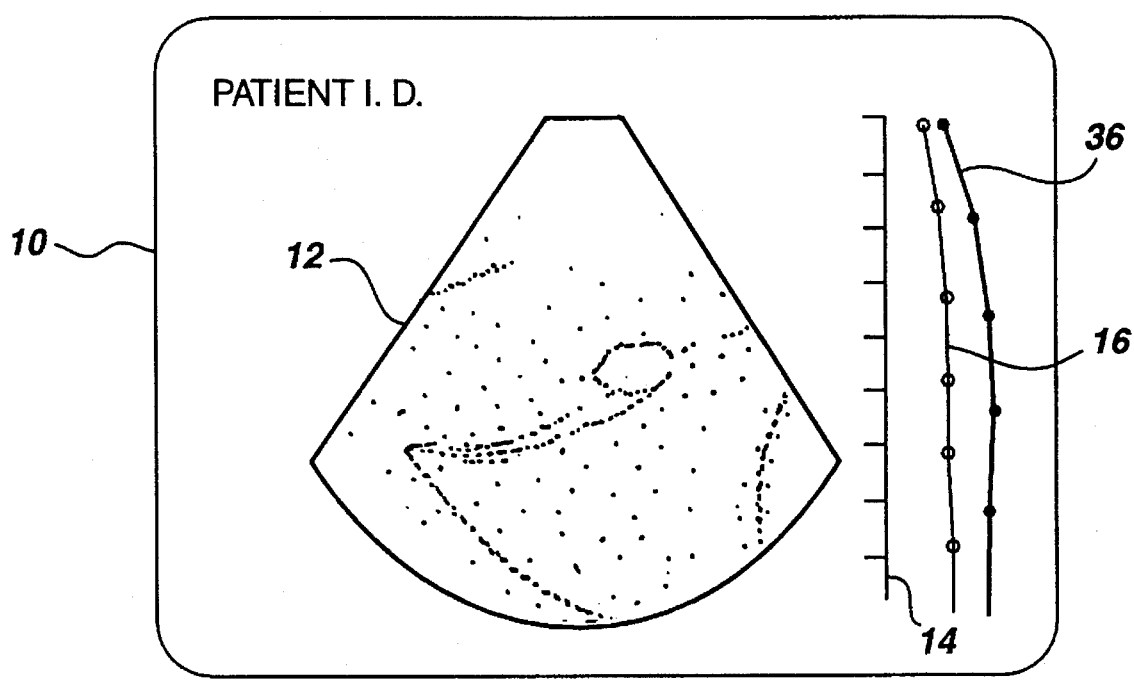

In the drawings:
FIG. 1 illustrates an ultrasonic image display with a displayed TGC characteristic;
FIG. 2 illustrates the user controls for varying the TGC characteristic in accordance with the principles of the present invention;
FIG. 3 is a block diagram of an ultrasound system which automatically provides predetermined TGC characteristics for various ultrasonic examination procedures in accordance with the present invention;
FIG. 4 illustrates the user controls of an ultrasonic diagnostic system; and
FIG. 5 illustrates an alternative technique for displaying the TGC characteristic on the ultrasonic image display in accordance with the present invention.

Referring first to FIG. 1, an ultrasonic image display 10 is shown. In the center of the display is the ultrasonic image 12 which shows the tissue structure or flow conditions of the patient being examined. In the upper left corner of the display is alphanumeric information concerning the patient and/or other characteristics of the examination being performed. To the right of the ultrasonic image 12 is a depth scale 14 aligned with the image, indicating the depth into the body to which the image extends. Usually the markers on the depth scale are calibrated in centimeters of depth.

To the right of the depth scale 14 is a graphic representation 16 of the TGC characteristic. The TGC characteristic is shown as a sequence of line segments joined by dots on the display. The relative slope of each line segment indicates the variation in gain applied to the received echo signals over the depth covered by that segment. Setting an individual TGC switch, as discussed below, will vary the slope of a respective line segment. Each line segment and its switch may have a predetermined, fixed depth over which it is effective, or the segments can be scaled in relation to the maximum depth of the particular image. An initial gain adjustment is used to offset the gain of the entire TGC characteristic, and causes the displayed characteristic 16 to move left or right as indicated by the arrow 18.

Each segment of the TGC characteristic is set by one of the TGC switches 20 shown in FIG. 2. Conventionally the TGC switches are slide switches such as indicated by the first switch 22 which slides horizontally along the groove 24. Switch 22 controls the gain over an initial depth portion of the image as indicated by the first segment 17 of the TGC characteristic 16. Moving slide switch 22 to the right will increase the gain over this initial depth, and will cause the first line segment 17 on the display to slope more quickly to the right. Turning a gain control adjustment 26 will cause the gain over the full depth to vary, and the TGC characteristic to move to the right or left as indicated by the arrow 18. When all the TGC switches 20 are vertically aligned along the center line 28 as shown in FIG. 2, there will be no variation in gain over the depth of the image and the TGC characteristic will appear as a straight vertical line over the full depth. If various ones of the TGC switches 20 are progressively moved to the right as shown on the user control console in FIG. 4, a progressively sloping TGC characteristic 16 as shown in FIG. 1 will result.

An ultrasound system which automatically sets the TGC characteristic is shown in FIG. 3. A scanhead 40 includes an array 42 of transducer elements which transmits ultrasonic waves and receives echoes under control of a transmitter/receiver 44. The received echo signals are amplified as a function of the depth from which they return by a TGC amplifier 50. In a practical embodiment of the present invention there is a separate TGC amplifier connected to receive echo signals from each individual element of the transducer array 42, and all of the separate TGC amplifiers are controlled simultaneously. The gain of the TGC amplifier or amplifiers 50 is controlled by a setup controller 70 which will be discussed more fully below. A beamformer 46 directs the timing of excitation of the transducer elements during transmission and provides appropriate delays to received echo components to produce a sequence of echo signals following each pulse transmission. The sequence of echo signals is filtered by a filter 52 and the echo signals are detected by a detector 54. The detected echo signals then undergo logarithmic compression by a log compression circuit 56 and are supplied to an image processor 60. The image processor 60 organizes the sequences of echo signals into an image format for display and also incorporates other information to be shown on the display such as patient identification information, a depth scale, and a TGC characteristic display. Much of this information is also supplied by the setup controller 70. The resultant image is then displayed on a display monitor 62.

When a user desires to perform a particular ultrasonic examination such as imaging the liver, the user selects the desired procedure by using the controls on the control panel 28, which is also shown in FIG. 4. This may involve interaction with a menu of parameters and performance choices shown on the display monitor 62. If the user selects abdominal scanning of the liver with a particular scanhead, this information is communicated to a setup memory 72 and a setup controller 70 from the control panel 28. The setup controller 70 then looks up the control parameters for such a procedure in the setup memory 72 and initializes the system to control the scanhead and echo signal processing specifically for this procedure. The beamformer will be set up by the setup controller to activate and receive echo signals from the selected scanhead, for instance. The setup memory also supplies information to the setup controller as to the optimal TGC characteristic to be used in scanning the liver. The setup controller 70 will then control the gain of the TGC amplifier 50 in accordance with this optimal TGC characteristic. The setup controller will also supply graphical information to the image processor 60 so that a visual representation 16 of the optimal TGC characteristic will be shown on the image display 62.

The optimal, predetermined TGC characteristic will be displayed and used to control the TGC amplifier 50 when the slide switches 20 are vertically aligned in their central position 28 as shown in FIG. 2. If the clinician finds that variation from the predetermined characteristic is needed to better image a particular patient, the clinician will move the slide switches to the right or left to reset the slope segments of the characteristic. As the switches are moved the changes are communicated from the control panel 28 to the setup controller, which applies the incremental changes to the predetermined characteristic. The effects of these changes are shown by visual changes to the displayed TGC characteristic through communication from the setup controller 70 to the image processor 60. When the clinician is finished adjusting the TGC switches 20 the variation from the predetermined characteristic is indicated by the new physical positions of the switches and the final TGC characteristic is shown on the display. A uniform gain adjustment over the full image depth is applied as before by adjusting the gain control adjustment 26.

If it is desirable for the physical positions of the switches 20 to constantly indicate the shape of the TGC characteristic 16 rather than variation from the predetermined setup TGC characteristic, the switches can be motor controlled by a motor 30 as indicated in FIG. 2. When the user selects a given procedure and the setup controller 70 sets up the operating characteristics of the system, the controller 70 will also issue commands to the motor 30 to automatically move the switches 20 to physical positions corresponding to the slopes of the segments of the TGC characteristic 16. The switches 20 would move under motor control from their initial alignment to the alignment representing the TGC characteristic, such as by moving to the alignment shown in FIG. 4. Thereafter the user would manually adjust the switches as before to alter the predetermined setup TGC characteristic.

An alternative technique for controlling and displaying the TGC characteristic is shown in FIG. 5. When the user selects a particular ultrasound examination procedure the setup controller operates as described above to control the TGC amplifier 50 in accordance with the predetermined setup TGC characteristic. The predetermined characteristic is also displayed as shown by the TGC characteristic 16 in FIG. 5. The setup characteristic is constantly displayed alongside the ultrasound image 12. If the user adjusts the TGC switches to create a different characteristic, the new characteristic is displayed in a highlighted display 36 along with the setup characteristic. Thus the user will see the preferred TGC characteristic and the modified TGC characteristic invoked for the particular examination.

With the display of both the initial and final TGC characteristics it may no longer be desired to use slide switches for the TGC switches 20. Instead, rocker switches can be used for the TGC switches. Pushing on the left side of a rocker switch will reduce the gain controlled by the switch and the slope of the corresponding TGC display line segment. Pushing on the right side of the rocker switch will increase the TGC gain and the slope of the line segment. Full control of the TGC gain characteristic is afforded through use of the gain control adjustment 26 and the rocker switches 20, and motor control is not necessary.

When the clinician has completed the ultrasound examination the clinician has the option of saving the TGC characteristic created for the particular examination of the patient. The final TGC characteristic can be saved in the setup memory along with the patient's name and the type of examination, such as a liver examination. If the clinician at a later date decides to reexamine the patient's liver, the clinician enters the patient ID from the control panel and selects a liver examination. The setup controller will then retrieve the previously stored TGC characteristic from the setup memory and use the information to apply the same TGC characteristic and display as previously determined by the clinician.

What is claimed is:

1. An ultrasonic diagnostic system including means for receiving a sequence of ultrasonic echo signals over a depth of scanning and means for controlling the amplification of said sequence as a function of depth comprising:

means for storing a plurality of predetermined time gain compensation characteristics;

processor means for selecting one of said predetermined time gain compensation characteristics in response to selection by a user of a particular ultrasonic diagnostic procedure;

amplifier means coupled to said processor means for controlling the amplification of said sequence of ultrasonic echo signals in accordance with said selected one of said predetermined time gain compensation characteristics; and means for displaying said selected one of said predetermined time gain compensation characteristics.

2. The ultrasonic diagnostic system of claim 1, wherein said means for displaying comprises a video display, and further comprising user adjustable TGC switch means for varying the time gain compensation characteristic used for controlling the amplification of said sequence of ultrasonic echo signals in relation to said selected one of said predetermined time gain compensation characteristics.

3. The ultrasonic diagnostic system of claim 2, wherein said user adjustable TGC switch means comprise a plurality of slide switches.

4. The ultrasonic diagnostic system of claim 2, wherein said user adjustable TGC switch means comprise a plurality of rocker switches.

5. The ultrasonic diagnostic system of claim 2, wherein said user adjustable TGC switch means further comprises means for visually indicating the variation of the time gain compensation characteristic used for controlling the amplification of said sequence of ultrasonic echo signals with respect to said selected characteristic.

6. The ultrasonic diagnostic system of claim 2, further comprising means for adjusting said user adjustable TGC switch means in response to the characteristic of a selected time gain compensation characteristic.

7. The ultrasonic diagnostic system of claim 6, wherein said user adjustable TGC switch means further comprises means for visually indicating the characteristic of said selected time gain compensation characteristic.

8. The ultrasonic diagnostic system of claim 2, further comprising means, coupled to said video display, for varying the displayed time gain compensation characteristic in response to adjustment of said user adjustable TGC switch means.

* * * * *